United States Patent [19]
Gunderson et al.

[11] Patent Number: 4,458,538
[45] Date of Patent: Jul. 10, 1984

[54] APPARATUS AND METHOD OF MEASURING EDGEWISE COMPRESSIVE DEFORMATION

[75] Inventors: Dennis E. Gunderson, Madison; Vance C. Setterholm, Blue Mounds, both of Wis.

[73] Assignee: The United States of America as represented by the Secretary of Agriculture, Washington, D.C.

[21] Appl. No.: 456,930

[22] Filed: Jan. 10, 1983

[51] Int. Cl.$^3$ ............................................. G01N 3/20
[52] U.S. Cl. ....................................... 73/854; 73/819
[58] Field of Search ................. 73/818, 819, 794, 795, 73/854

[56] References Cited

U.S. PATENT DOCUMENTS 3,164,010  1/1965  Jones ..................................... 73/819
3,636,758  1/1972  McKee et al. ......................... 73/794

OTHER PUBLICATIONS

Franks, R. et al., The Stress-Strain . . . Cylinder Test Method, 1941, ASTM Proceedings, pp. 629-645, vol. 41.
Setterholm, V. et al., Method for Measuring . . . Paper, May 1965, Tappi, vol. 48, No. 5, pp. 308-313.
Stockmann, V., Measurement . . . Compressive Strength of Paper, Jul. '76, Tappi, vol. 59, No. 7, pp. 93-97.
Tappi Test T818 OM-82, Ring Crush of Paperboard, 1982.
Fellers, C. et al., Compression Strength of Linerboard . . . Methods, 1975, Svensk Papperstidning, vol. 78, No. 5, pp. 172-175.
Jackson, C. et al., Edgewise Compressive . . . Method, Oct. '76, vol. 77, No. 10, Pulp and Paper Canada, pp. 43-46.
Seth, R. et al., An Evaluation . . . Strength of Paper, Oct. '79, Tappi, vol. 62, No. 10, pp. 125-127.
Ramberg, W. et al., Determination . . . Thin Sheet Metal, 1946, J. of Aeronautical Sciences, pp. 569-580.
Calvin, S. et al., A method for . . . Properties of Paper, Svensk Papperstidning, vol. 78, No. 9, pp. 330-333.
Gunderson, D., A Method for Compressive . . . Paperboard, Nov. '81, Tappi, vol. 64, No. 11, pp. 67-71.
North American Rockwell Corporation, Structural Design Guide . . . Composite Applications, Aug. '69, USAF Contract F33615-69-C-1368.
Lauraitis, K. N., Fatigue of Fibrous Composite Materials, 1981, ASTM Special Technical Publication 723.
Tsai, S. W. et al., Composite Materials Workshop, 1968, Technomic Publishing Co., Stamford Conn., pp. 254-258.
Whiteside, J. B. et al., The Behavior . . . Composite Plates with Cutouts, June '73, USAF Technical Report AFFDL-TR-73-48, pp. 64 and 69.
Shuart, M. J. et al., Tensile and Compressive . . . Matrix Composites, 1977, VPI-E-77-6 Report VPI College, Blacksburg, Va.
Lenoe, E. M., Testing and Design of Advanced Composite Materials, 1970, Journal of American Society of Civil Engineers, pp. 809-823.

Primary Examiner—Jerry W. Myracle
Attorney, Agent, or Firm—M. Howard Silverstein; David G. McConnell

[57] ABSTRACT

An apparatus and method of measuring edgewise compressive deformation in sheet material comprises providing a specimen beam having an inner curved layer of the sheet material to be tested, an outer curved strip spaced radially outwardly of the sheet material, an elastomeric spacer between the sheet and strip, and blocks fixing the opposite ends of the sheet material to the opposite ends of the strip. The spacer is fixed to the backing strip and engaged firmly on the outer radial surface of the sheet material. The ends of the curved specimen beam receive a pure torque which causes compression of the sheet material which can be measured. The sheet material is supported so that it does not buckle with the torque being applied by simple weights connected to rotors which in turn are engaged with the opposite ends of the specimen beam.

13 Claims, 7 Drawing Figures

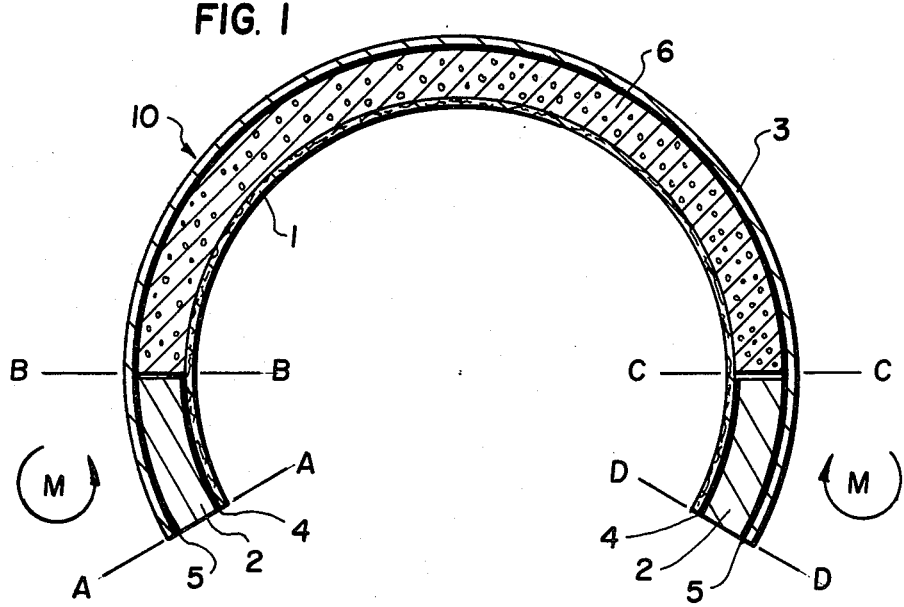
FIG. 1
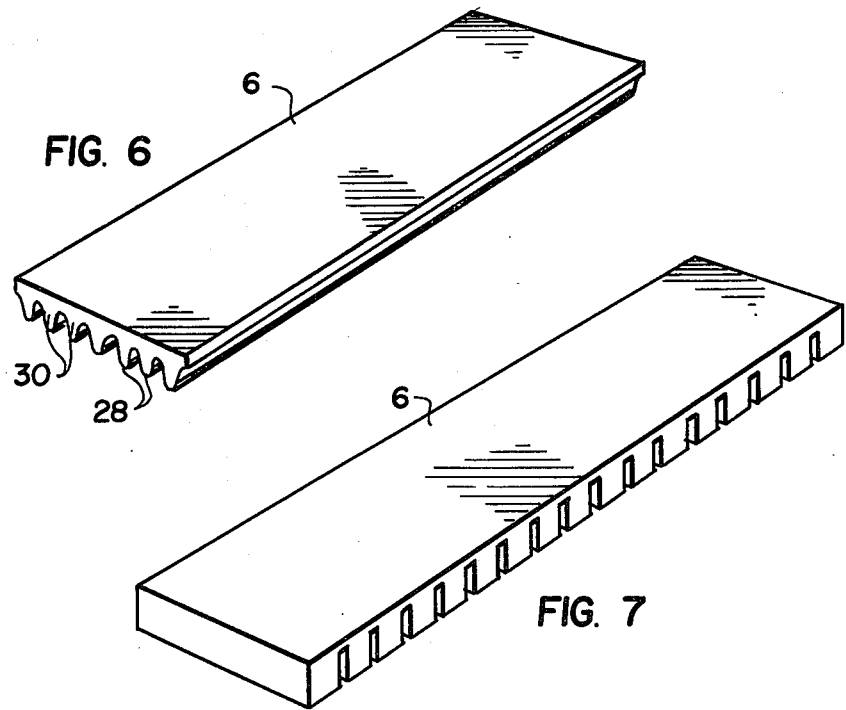
FIG. 6
FIG. 7

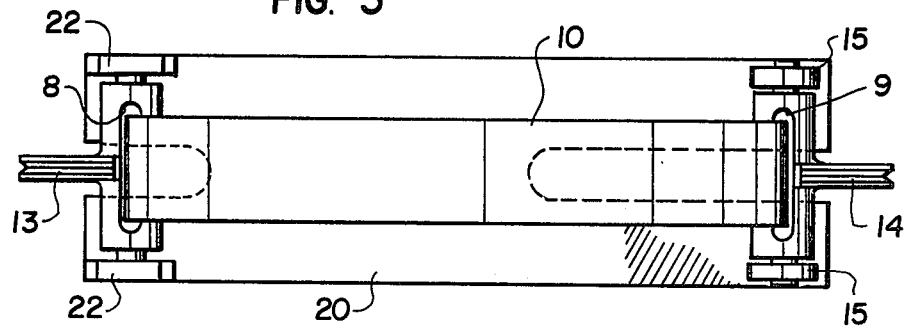
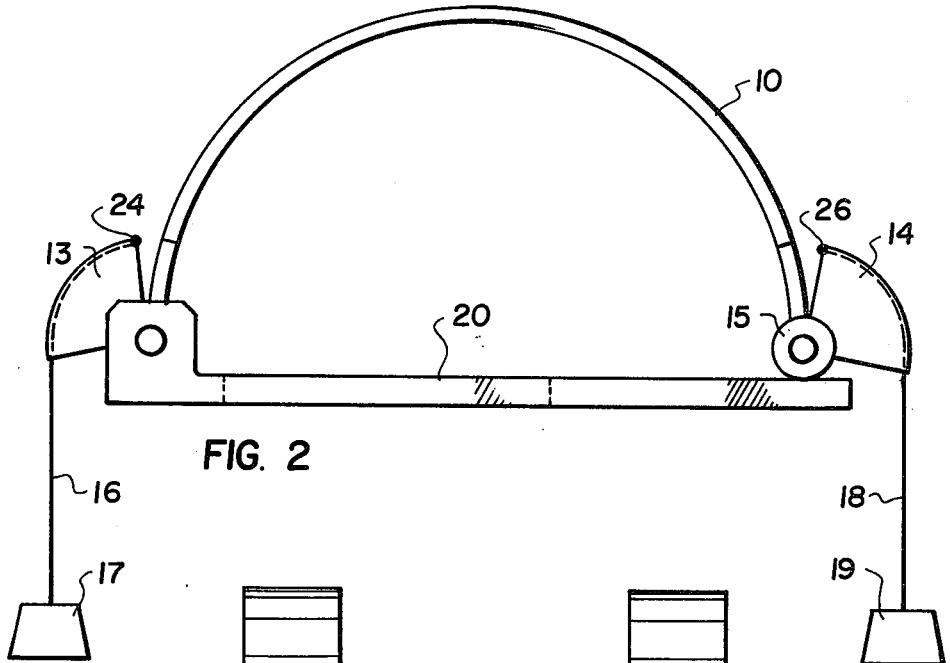
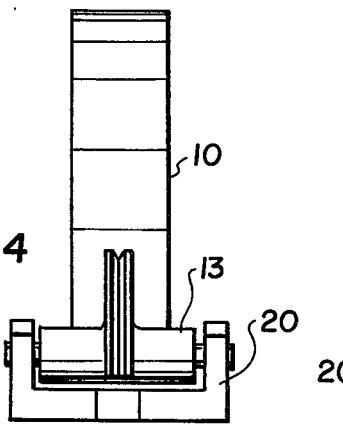
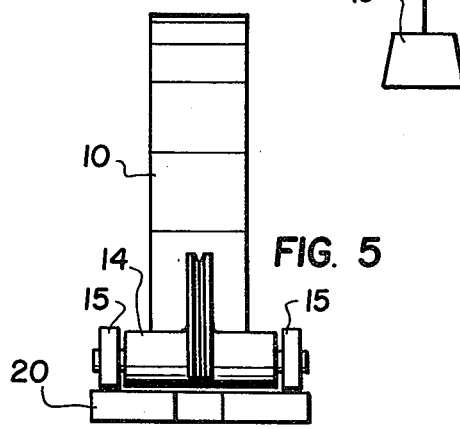

APPARATUS AND METHOD OF MEASURING EDGEWISE COMPRESSIVE DEFORMATION

BACKGROUND OF THE INVENTION

1. Field of the Invention

This invention relates to the measurement of edgewise compressive deformation (creep) of paperboard or other sheet materials, during extended durations of load.

2. Description of the Prior Art

Edgewise compressive deformations is of particular importance in paperboard materials which are used to make corrugated paperboard containers. Evaluation of edgewise compressive properties in sheet materials requires not only means to apply the uniform compressive loads, but also means to provide lateral support to prevent buckling of the test specimen. The method currently used for evaluation of creep require an expensive apparatus and a continuous vacuum source. For this reason, it is not practical to consider evaluating large numbers of specimens at one time. It is also not practical to evaluate material behavior in actual warehouse environements.

Prior art approaches to the problem of measuring compressive behavior can be found in the following references:

Franks, R., and Binder W. O. (1941), "The Stress-Strain Characteristics of Cold-Rolled Austenitic Stainless Steels In Compression As Determined By The Cylinder Test Method", *ASTM Proceedings* 41; 629.

Setterholm, V. C., and Gertjejansen, R. O. (1965), "Method For Measuring The Edgewise Compressive Properties Of Paper", *Tappi* 48 (5): 308.

Stockman V. (1976), "Measurement Of Intrinsic Compressive Strength Of Paper", Tappi 59 (7): 93. *Tappi Standard* T 818 OM82 (1982) Ring Crush of Paperboard.

Fellers, C., and Jonsson, P. (1975), "Compression Strength of Linerboard And Corrugated—An Analysis Of Testing Methods", (Swedish), *Svensk Papperstidning* 78(5): 172.

Jackson, C. A., Koning, J. W., and Gatz, W. A. (1976), "Edgewise Compressive Test of Paperboard By A New Method", *Pulp and Paper Magazine of Canada* 77(10): T 180.

Seth, R. S., and Sosynski, R. M. "The Intrinsic Edgewise Compressive Strength Of Paper: An Evaluation Of Methods", *Tappi* 62(10): 125.

Ramberg, W., and Miller, J. A. (1946), "Determination And Presentation Of Compressive Stress-Strain Data For Thin Sheet Metal", *J. of Aeronautical Sciences* 13(11): 569.

Calvin, S., and Fellers, C. (1975), "A New Method For Measuring The Edgewise Compression Properties Of Paper", *Svensk Papperstidning* 78(9): 330.

Gunderson, D. E. (1981), "A Method For Compressive Creep Testing of Paperboard", *Tappi* 64(11): 67.

North American Rockwell Corporation, (1969), "Structural Design Guide For Advanced Composite Applications", U.S. Air Force Contract F 33615-69-C-1368.

Lauraitis, K. N. (1981), "Fatigue Of Fibrous Composite Materials", *ASTM Special Technical Publication* 723, ASTM, Philadelphia, Pa.

Tsai, S. W., Halpin, J. C., and Pagano, N. J. "Composite Materials Workshop", Technomic Publishing Co., Stamford, Conn.

Whiteside, J. B., Daniel, I. M., and Rowlands, R. E. (1973), "The Behavior Of Advanced Filamentary Composite Plates With Cutouts", *U.S. Air Force Systems Command Technical Report* AFFDL-TR-73-48.

Stuart, M. J., and Herakovich, C. T. (1977), "Tensile and Compressive Test Results for Metal Matrix Composites", VPI-E-77-6 Virginia Polytechnic Institute and State University.

Lenoe, E. M. (1970), "Testing And Design Of Advanced Composite Materials," *J. of the Eng. Mechanics Div., Proceedings of the Amer. Soc. of Civil Engineers.*

The first problem encountered in attempting to measure the compression creep properties of a thin sheet material such as paperboard is that the sheet will buckle at very light loads. A number of methods and devices have been proposed and developed to overcome this problem. These methods involve six general approaches outlined below and described in the above cited references:

1. The sheet is rolled into a tube and provided with internal support.
2. The span (length of specimen) between the supports is shortened to the point where buckling does not occur.
3. The sheet is restrained between two flat plates.
4. The sheet is restrained between an array of fingers on each side of the sample. These fingers deflect with the sample as it undergoes strain in the direction of loading-but provide restraint against lateral (out of plane) motion.
5. The sheet is held in contact with a planar surface by a pressure difference.
6. The sheet is laminated with other materials to form a straight composite beam. Lateral support is provided by gluing the specimen to the composite over its entire length.

The method described here is different in concept from all other methods known to the inventors. A uniform lateral force component (normal to the surface of the sheet) is generated as a result of the edgewise compressive force applied to the sheet and the curvature of the composite beam design. This lateral force component forces the sheet in contact with the elastomer and prevents buckling of the sheet. The tensile forces in the steel backing cause it to form a smooth arc and oppose any tendency to waviness or buckling. The sheet being tested is not glued to the other components in its active region as is necessary in a flat composite beam. The method requires a simple means of applying a pure moment loading. It does not require complex and costly fixtures to provide lateral support. Deformation of the specimen, due to compressive creep, results in a reduction in the radius of curvature of the composite beam-of which the specimen is a part. Because of the rigid design of the end portions of the composite beam, the radius of curvature can be directly related to specimen deformation. Small amounts of creep deformation in the specimen sheet are manifest as large changes in radius of curvature, or diameter, of the composite beam and can, therefore, be measured with a common ruler. Measurements can be made at desired intervals of time without maintaining a continuous reference.

SUMMARY OF THE INVENTION

The present invention comprises a method and apparatus for measuring edgewise compressive deformation.

Major advantages of this invention are that the equipment is very simple and there is no need for support utilities. Consequently, it is reasonable to consider evaluating large numbers of specimens in circumstances not previously practical. Moreover, deformation can be measured at desired intervals of time without maintaining a continuous physical reference as required under present methods.

Accordingly, an object of the present invention is to provide a method of measuring lengthwise compressive deformation in sheet material comprising: providing a specimen beam having an inner curved layer of the sheet material to be tested, an outer curved backing strip spaced radially outwardly of the sheet material, an elastic spacer between the inner sheet material and the outer strip fixed to the outer strip and slidably engaged against the inner sheet material, and load blocks fixed between opposite ends of the sheet material and respective opposite ends of the strip;

applying a pure torque to the load blocks in a direction to reduce a radius of curvature of the specimen beam; and measuring an amount of compression of the sheet material due to a reduction in the radius of curvature of the specimen beam.

Another object of the present invention is to provide an apparatus for measuring edgewise compression which comprises a base, a first rotor rotatably mounted at a fixed location on said base for receiving one end of the specimen beam, a rotor mounted for pivotal and translational motion with respect to said base for receiving an opposite end of the specimen beam and weights connected to said rotors for applying a pure torque to the opposite ends of the specimen beam.

A still further object of the invention is to provide a specimen beam for measuring edgewise compressive deformation of sheet material comprising, a curved sheet of the sheet material to be tested, a curved backing strip spaced radially outwardly from the curved sheet, a load block fixed to each end of the curved sheet and between the curved sheet and the backing strip, and an elastic spacer between the sheet and strip fixed to the strip and slidably engaged against the outer radial surface of the sheet.

A still further object of the invention is to provide an apparatus and specimen beam for measuring creep which are simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 1 is a side sectional view of a specimen beam according to the present invention;

FIG. 2 is a side elevational view of an apparatus for measuring creep in accordance with the invention;

FIG. 3 is a top plan view of the apparatus shown in FIG. 2;

FIG. 4 is a side elevational view of the apparatus shown in FIG. 3;

FIG. 5 is a side elevational view of the apparatus shown in FIG. 3 taken from a side opposite FIG. 4;

FIG. 6 is a perspective view of an elastic or elastomeric spacer used in accordance with the invention; and FIG. 7 is a perspective view similar to FIG. 6 of another embodiment of the spacer.

DESCRIPTION OF THE PREFERRED EMBODIMENT

Referring to the drawings in particular, the invention embodied therein comprises a method and apparatus of measuring creep or edgewise compressive deformation for sheet material, in particular paperboard.

FIG. 1 illustrates the preparation of a test specimen 1, to be used with the invention and its fabrication into a curved composite beam 10. The ends of specimen 1 (those portions from planes AA to BB, and CC to DD) are impregnated with a rigid epoxy or other resin and cured. The strength and impermeability of the epoxy renders the ends stronger, stiffer, and more dimensionally stable than the untreated central portion of the specimen (that part from plane BB to CC).

The prepared specimen 1 is then bonded to load blocks 2 with a rigid adhesive 4. While the specimen 1 is held in a curved shape, as shown, a flexible elastomer spacer 6 is fitted over the specimen 1, but not bonded to it. Fabrication is completed by bonding a thin metal backing strip 3 to the load blocks 2 and the elastomer spacer 6 with a rigid adhesive 5.

Application of a pure torque M to both of the loading blocks 2 creates a constant bending moment in the "active" portion of the beam from BB to CC. Under this condition of loading, backing 3 is subjected to uniform tension from BB to CC and the untreated portion of the specimen 1 is subjected to uniform compression from BB to CC. Brom BB to CC, backing 6 and specimen 1 are the only components capable of carrying significant load. This can be verified experimentally by bending tests of composite beams in which either specimen 1 or the backing 3 are severed. The function of the elastomeric spacer is to maintain a constant spacing between the backing 3 and test specimen 1. At the instant the bending moment is first applied to the beam, both the backing 3 and the specimen 1 deform elastically in the region from BB to CC contributing to the initial curvature of the beam between these planes. There is essentially no deformation in the rigid end portions. Subsequent changes in curvature over the duration of the creep test are the result of creep deformation of the specimen 1 alone, because the steel backing 3 is not subject to creep deformation under load, and because there is no further elastic deformation since the test is conducted at a constant bending moment, hence, constant stress.

It is well known that a thin member such as the test specimen 1 is highly susceptible to buckling at low levels of compressive load. Because the beam is formed in a curved shape, first application of edgewise compressive load creates a uniform component of normal force which holds the test specimen 1 in contact with the elastomeric spacer 6 over the full active length of the specimen to inhibit buckling. Buckling of the compressive member is thus restricted by uniform lateral forces which are transmitted to the backing 3 through the elastomeric spacer 6. Buckling deformation of the thin backing 3 is opposed by the longitudinal tensile forces created in it by the moment applied to the beam.

Creep deformation of the test specimen can be read directly on the specimen by means of moire methods which are well known in the stress analysis field. Creep deformation may also be related to changes in the radius of curvature of that portion of the beam between BB and CC according to the following formula:

$$\text{Creep} = \frac{R_1 y \frac{R_2 - R_1}{R_1 R_2} 100}{R_1 - y}$$

where:
y = beam thickness $$- \frac{\text{backing thickness}}{2} - \frac{\text{specimen thickness}}{2}$$

$R_1$ = radius of curvature after initial application of bending moment (measured at the steel backing)
$R_2$ = radius of curvature after extended period of load In this formula, creep is expressed in percent relative to the original specimen length after elastic deformation. Radius of curvature can be evaluated by any of several well known means in the art. If the active portion of the beam (that portion from BB to CC) subtends more than 180°, the radius of curvature can be determined by measurement of the specimen diameter with a ruler. It is significant that creep can be measured without the continuous use of strain measuring intrumentation as required by present methods.

FIGS. 2 through 5 illustrate the application of load by means of a moment or torque applied equally to both ends of the beam. Part numbering is consistent in FIGS. 2 through 5.

Referring to the side view, FIG. 2 and the plan view, FIG. 3, it can be seen that the fabricated composite beam 10 is dropped into slots 8,9 in a stationary rotor 13 on the left and translating rotor 14 on the right. Rotor 13 is free to rotate in supports which are integral with a base 20. Rotor 14 is fitted with a pair of wheels 15 which allow it to rotate and also translate horizontally along the base 20.

Pure torque is applied to the composite beam 10 by means illustrated in FIG. 2. A cord 16 is attached to the stationary rotor 13 at point 24 at the upper end of the integral pulley sector of rotor 13. The cord 16 rests in the groove of the pulley sector. A weight 17 is attached to the other end of the cord 16. The torque applied to the beam 10 is the product of the weight 17 times the distance from the rotational center of the rotor 13 to the point where the cord 16 becomes tangent to the pulley segment of rotor 13. Note that this distance remains constant with rotation of the rotor 13 so that the applied torque remains constant despite deformation of the composite beam 10. A similar configuration is employed at the translating rotor 14. Cord 18 is attached at the upper end of the integral pulley segment of rotor 14 at point 26. A cord 18 lies in the groove of the pulley segment. Weight 19 (equal in mass to weight 17) is attached to cord 18 at its other end.

The torque applied to the right end of the composite beam 10 is the product of the weight 19 times the distance from the rotational center of rotor 14 to the point where the cord 18 becomes tangent to the pulley segment of rotor 14. This distance remains constant with rotation or translation of rotor 15. Consequently, the torque applied to the composite beam remains constant and thus independent of beam deformation.

FIG. 4 illustrates the position of stationary rotor 13 in the bearing supports of the base 20. FIG. 5 shows the freely rotating wheels 15 on the translating rotor 14. Wheels 15 rotate relative to rotor 14 and roll freely along base 20.

Alternate designs of the elastomeric spacer may also be employed to evaluate the effect of support spacing on creep of the test specimen or to reduce the effect of elastomer stiffness in tests where the radius of curvature is small.

FIG. 6 shows an elastomeric spacer 6 designed to provide lateral support in a manner analagous to that provided to the linerboard by the corrugating medium in corrugated containers. Contact of the test specimen with the tips 28 of the flutes 30 provides continuous support in the longitudinal direction and interrupted support in the transverse direction.

FIG. 7 illustrates means of relieving the elastomeric spacer 6 on its compression side to render it more flexible at small radii.

Fabrication of the test specimen into a curved beam composed of rigid and elastomeric materials is a new approach to creep testing of paperboard or other sheet materials. The structure described here creates a beam in which the test specimen is subjected to uniform compressive stress and is supported laterally to prevent buckling. This unique design provides the required lateral support without the use of supplemental mechanical fixtures or devices or bonding of the specimen to the support. The combination of a creep-free tensile member and extremely rigid end segments creates conditions which permit creep to be related to the radius of curvature of the "active" portion of the beam. The design of the test specimen amplifies the effect of deformation. Very small amounts of creep are manifest in large changes in radius which can be measured with a ruler. One face of the test specimen is also fully exposed for strain measurement by optical methods. (e.g. moire) if desired.

The composite beam is self-stabilizing. Complex and costly test fixtures to provide lateral support to the compressive test specimen are not needed. Consequently, it is practical to consider testing large numbers of specimens for greatly extended periods. The effect of alternative lateral support configurations can be evaluated by varying the design of the elastomeric spacer.

The apparatus designed for application of the pure torque M to the load blocks of the composite beam is unique in its simplicity. The design allows the beam to be dropped into place without adjustment or clamping. The apparatus applies a precise pure torque to each end of the beam while permitting large lateral and rotational deformations and yet requires a small number of easily fabricated, inexpensive parts.

While a specific embodiment of the invention has been shown and described in detail to illustrate the application of the principles of the invention, it will be understood that the invention may be embodied otherwise without departing from such principles.

What is claimed is:

1. A method of measuring edgewise compressive deformation of sheet material comprising:
   providing a specimen beam having an inner curved layer of sheet material to be tested, an outer curved backing strip spaced radially outwardly of the sheet material, an elastic spacer between the sheet material and backing strip fixed to the strip and slidably engaged against the sheet material, and load blocks fixed between opposite ends of the sheet material and respective opposite ends of the backing strip;

applying a pure torque to the load blocks in a direction to reduce a radius of curvature of the specimen beams; and measuring an amount of compressive deformation for the curved sheet material.

2. A method according to claim 1, including connecting the load blocks to the sheet material and backing strip and connecting the elastic spacer to the backing strip using rigid adhesive.

3. A method according to claim 1, wherein the sheet material is paperboard.

4. An apparatus for measuring edgewise compressive deformation of sheet material comprising a specimen beam having an inner layer formed of the sheet material to be tested, an outer backing strip fixed to opposite ends of the sheet material and an elastic spacer between the sheet material and the backing strip;

a base;

a first rotor rotatably mounted at a fixed location on said base, means for connecting one end of said specimen beam to said first rotor;

a second rotor rotatably translationally mounted on said beam at a position spaced from said first rotor;

means for connecting an opposite end of said specimen beam to said second rotor; and weights connected to said first and second rotors for applying a torque thereto.

5. An apparatus according to claim 4, wherein said means for connecting ends of said specimen beam to said first and second rotors comprise a slot in each of said first and second rotors for receiving an end of said specimen beam.

6. An apparatus according to claim 4, wherein said second rotor includes a pair of wheels for rolling engagement on said base.

7. An apparatus according to claim 4, wherein each of said first and second rotors are in the form of a pully segment having a constant radius, and a cord connected between a top of each pulley segment and said weight so that constant force is applied to each rotor independent of a radial position of each rotor with respect to said base.

8. A device according to claim 4, including a slot in said base on a side thereof adjacent said first and second rotors, said second rotor including a pair of wheels engaged on said base on opposite sides of one slot.

9. An apparatus as described in claim 4 wherein the sheet material and the backing strip are curved and which further includes load blocks fixed between opposite ends of the sheet material and respective opposite ends of the backing strip, wherein said load blocks comprises the means by which said outer backing strip is fixed to said sheet material.

10. A specimen beam according to claim 9, wherein said sheet material comprises paperboard.

11. A specimen beam according to claim 9, wherein said backing strip is made of sheet metal.

12. A specimen beam according to claim 9, wherein said elastic spacer is corrugated in a circumferential direction around said curved sheet and backing strip, with longitudinal grooves facing said curved sheet.

13. A specimen beam according to claim 9, wherein said elastic spacer includes grooves which are transverse to a radial direction of said curved sheet and backing strip.

* * * * *